United States Patent
Davoine et al.

(10) Patent No.: US 9,946,019 B2
(45) Date of Patent: Apr. 17, 2018

(54) GUIDED MODE RESONANCE DEVICE

(71) Applicants: Laurent Davoine, Saint-Louis (FR); Guillaume Basset, Huningue (FR)

(72) Inventors: Laurent Davoine, Saint-Louis (FR); Guillaume Basset, Huningue (FR)

(73) Assignee: CSEM CENTRE SUISSE D'ELECTRONIQUE ET DE MICROTECHNIQUE SA—RECHERCHE ET DÉVELOPPEMENT, Neuchâtel (CH)

(*) Notice: Subject to any disclaimer, the term of this patent is extended or adjusted under 35 U.S.C. 154(b) by 61 days.

(21) Appl. No.: 15/106,723

(22) PCT Filed: Dec. 23, 2013

(86) PCT No.: PCT/EP2013/077956
§ 371 (c)(1),
(2) Date: Jun. 20, 2016

(87) PCT Pub. No.: WO2015/096859
PCT Pub. Date: Jul. 2, 2015

(65) Prior Publication Data
US 2016/0356956 A1 Dec. 8, 2016

(51) Int. Cl.
*G01N 21/77* (2006.01)
*G02B 6/124* (2006.01)
(Continued)

(52) U.S. Cl.
CPC ......... *G02B 6/124* (2013.01); *G01N 21/7743* (2013.01); *G02B 5/1809* (2013.01);
(Continued)

(58) Field of Classification Search
CPC .................................................. G01N 21/77
(Continued)

(56) References Cited

U.S. PATENT DOCUMENTS 5,071,248 A * 12/1991 Tiefenthaler ......... G01N 21/431
356/128
5,738,825 A 4/1998 Rudigier et al.
(Continued)

FOREIGN PATENT DOCUMENTS

EP 1 031 828 A1 8/2000
EP 1 990 661 A1 11/2008
WO 2011/144652 A2 11/2011

OTHER PUBLICATIONS

International Search Report dated Sep. 11, 2014, issued in corresponding International Application No. PCT/EP2013/077956, filed Dec. 23, 2013, 3 pages.

*Primary Examiner* — Arlen Soderquist
(74) *Attorney, Agent, or Firm* — Christensen O'Conner Johnson Kindness PLLC

(57) ABSTRACT

A guided mode resonance device, comprising—a substrate,—a waveguide,—a grating structure associated with said waveguide, said grating structure being arranged to an incident surface of said substrate, said incident surface being intended to receive an incident light beam provided by at least one light source, said incident light beam having an incident angle, defined relative to the normal of said waveguide, said grating structure comprising at least one elementary structure comprising at least a first-type grating structure and at least a second-type grating structure,—wherein:—said waveguide is arranged to transfer light from the first-type grating structures to the second-type grating structure and also to transfer light from the second-type grating structures to the first-type grating structure,—said first-type grating structure is arranged to couple out a first light beam,—said second-type grating structure is arranged to couple out a second light beam,—said first light beam having a different spectral distribution than said second light beam.

15 Claims, 10 Drawing Sheets

(51) Int. Cl.
  *G02B 5/20* (2006.01)
  *G02B 6/12* (2006.01)
  *G02B 5/18* (2006.01)
  *G02B 6/293* (2006.01)
  *G02B 6/34* (2006.01)
  *G02B 27/42* (2006.01)

(52) U.S. Cl.
  CPC ......... *G02B 5/203* (2013.01); *G02B 6/12007* (2013.01); *G02B 6/29325* (2013.01); *G02B 6/34* (2013.01); *G02B 27/4272* (2013.01); *G02B 2006/12107* (2013.01)

(58) Field of Classification Search
  USPC ............................ 422/82.05, 82.11; 436/165
  See application file for complete search history.

(56) References Cited

U.S. PATENT DOCUMENTS

| | | | |
|---|---|---|---|
| 6,483,096 B1 * | 11/2002 | Kunz | G01N 21/6428 250/214 R |
| 9,478,713 B2 * | 10/2016 | Cunningham | H01L 33/50 |
| 2003/0002156 A1 * | 1/2003 | Hobbs | G02F 1/133371 359/573 |
| 2003/0210396 A1 * | 11/2003 | Hobbs | G02B 1/005 356/416 |
| 2005/0025422 A1 * | 2/2005 | Magnusson | B82Y 30/00 385/37 |
| 2006/0024013 A1 * | 2/2006 | Magnusson | G02B 6/124 385/129 |
| 2006/0040376 A1 * | 2/2006 | Cunningham | B01L 3/5085 435/287.1 |
| 2008/0062418 A1 * | 3/2008 | Magnusson | G01N 21/253 356/307 |
| 2011/0267623 A1 | 11/2011 | Matejka et al. | |
| 2013/0005605 A1 * | 1/2013 | Chakravarty | G01N 33/54373 506/9 |
| 2013/0288357 A1 | 10/2013 | Tiefenthaler | |
| 2015/0258835 A1 * | 9/2015 | Fischer | B42D 25/328 356/71 |
| 2016/0274281 A1 * | 9/2016 | Lutolf | G02B 5/1852 |

* cited by examiner

GUIDED MODE RESONANCE DEVICE

TECHNICAL FIELD

The invention relates to the field of optical devices, more particularly to devices that incorporate optical waveguides. It more specifically relates to guided mode resonance devices and their application in optical sensors, optical filters and security devices.

BACKGROUND OF THE INVENTION

The field of thin-film optics is an important area in optical technologies. A huge variety of filters and optical devices are produced and used in numerous industries and for a wide range of applications. Most of these thin-film optical structures, assemblies and devices consist of homogeneous layers deposited with precisely controlled thicknesses and material parameters and they are most often realized in a low pressure atmosphere needing a sophisticated technology. Examples of devices using such multilayer filters include, but are not limited to, antireflection filters, low-and high pass filters, phase plates, flat beamsplitters, polarization filters, micromirrors. In several of these devices thin film optical structures may be arranged so that their combination widens the potential use of these devices.

A significant drawback associated with these thin-film optical devices is that very often a large number of layers are needed to obtain a significant optical effect. It is not exceptional that the required number of stacked layers is higher than 50. These optical devices function mainly by multiple reflections between the interfaces of the different stacked layers of the device. The complexity of the technology to master the optical quality of such devices can be considerably high and is thus expensive. Also, adhesion and stability problems associated with multiple stacked layers may be a problem. Scattering effects and unwanted reflections inside the optical stack are a current problem especially if special optical effects are to be obtained such as occurring in high quality filters, interferometry or high power laser applications where any stray light may be a limiting factor.

Gratings have also been used widely as devices to disperse and filter optical beams. The combination of gratings and waveguides has been proposed to make optical structures and devices with unique properties such as filters having very narrow bandwidths. More particularly a considerable amount of development work has been made in the field of resonating waveguide gratings as they allow producing particularly interesting optical effects that cannot be realized with classical optical components.

A resonant waveguide grating, also called guided-mode resonance filter, consists of a combination of a sub-wavelength grating and a thin film waveguide. Such structures have a multilayer configuration and a basic arrangement comprises a substrate, a thin dielectric or semiconductor waveguide layer and possibly an additional layer in which a grating is formed. A so-called resonance occurs when the incident light is diffracted by the grating and matches a mode of the waveguide. As most of the spectrum does not couple into the waveguide, strong spectral changes are observed in reflection and transmission. The existence of such resonances has been discovered in the earlier stages of grating developments (R. W. Wood, Phil. Mag. vol 4, pp. 396-402, 1902). These resonances belong to one type of the anomalous diffraction phenomena in grating structures and imply a rapid variation in the external observable diffracted orders with respect to physical parameters such as the angle and/or the wavelength of the incident wave. In the early stages of grating manufacturing the abrupt change of reflection could not be explained. Hessel and Oliner (Appl. Optics, vol. 4, pp. 1275-1297, 1965) pointed out that there are basically two types of grating anomalies. One is called the Rayleigh type, which is the classical Wood's anomaly, and another is called the resonance type. The Rayleigh-type anomaly is owing to the energy of higher diffracted order transferred to an evanescent wave.

The resonance anomaly in diffraction gratings, being of particular interest in the context of the current patent application, is due to the coupling process of externally incident wave to a surface guided wave which is supported by the structure. Such grating anomalies can be divided into two types in function of the type of the structure and accurate results can be obtained by using the Fourier-Rayleigh approximation. This method cannot be applied in the case of deep grating grooves. Several authors investigated the reflection from weakly corrugated waveguides. The convergence problems of deep grating grooves could be relaxed by using the rigorous simulation methods such as the Fourier-Modal-Method (FMM) or the Rigorous Coupled-Wave Analysis (RCWA). With these new mathematical tools, many devices have been proposed and developed the last decade.

One of the main applications of guided mode resonance structures has been the design of filters with very narrow spectral linewidths in reflection and transmission. The bandwidth can be designed to be extremely narrow and of the order of 0.1 nm and may be tuned by parameters such as the grating depth, the duty cycle and the thickness of the waveguide layer. Magnusson proposed wavelength selective reflection filters and investigated their line shapes (R. Magnusson and S. S. Wang: "New principle for optical filters", Appl. Phys. Lett., vol. 61, pp. 1022-1024, 1992). Also, a systematic analysis of resonant grating waveguide structures has been published by Rosenblatt and Sharon:

D. Rosenblatt et al., "Resonating grating waveguide structures", IEEE J. Quantum Electron., vol. 33, nr. 11. pp. 2038-2059, 1997;

A. Sharon et al.: "Resonating grating-wavegudie structures for visible and near-infrared radiation:", J. Opt. Soc. Am., vol. 14, nr. 11, pp. 2985-2993, 1997.

Rosenblatt and Sharon explained in these papers that the efficient transfer of wave energy between forward and backward propagations at resonance is due to the relative phase-shift between the incident and the diffracted waves, resulting in destructive and constructive interference of forward and backward propagating waves.

Limitations of resonating waveguide structures are particularly linked with the fact that specular reflection phenomena reduce the performances of filters. These specular reflection effects may also limit the performance of resonating waveguide structures when they are used to produce specific colors. The color hue is limited by internal reflection effects and/or by effects due to specular reflection.

Guided mode resonance devices may also be used as components in sensors. By applying a substance such as a gas or a bio-chemical layer in contact with the resonating waveguide, these substances may be detected. A limitation of guided mode resonance devices in sensors is that the interaction length of the waves interacting with said substances is limited and thus the effects obtained are small.

An example of use of a resonating waveguide-grating as a sensor to detect the presence of a gas is described in the article of L. Davoine et al.: "Resonant absorption of a chemically sensitive layer based on waveguide gratings", Applied Optics, pp. 340-349, vol. 52, nr. 3, 2013. In such a device the major drawback is the inherent leakage of light along the waveguide, therefor the resonant light cannot be absorbed completely. In addition a delicate trade-off has to be chosen between a possible absorption enhancement and the resonance bandwidth of the resonating waveguide-structure.

SUMMARY OF THE INVENTION

The object of the present invention is to overcome at least partially the limitations of guided mode resonance devices as described in the prior art, and thereby to provide a guided mode resonance device having an improved optical light management performance. Another object of the invention is to improve the performance of such guided mode resonance devices used as a main component in gas and bio-chemical sensor devices, as well as used as a security device.

To this end the invention concerns a guided mode resonance device based on resonant waveguide gratings on which at least two gratings are arranged that communicate with each other by exchanging light provided by an incident light beam on said at least two gratings. By exchanging light, the at least two gratings produce at least two outcoupled light beams having a different spectral distribution.

The object of the invention is more precisely achieved by a guided mode resonance device comprising:
  a substrate,
  a waveguide,
  a grating structure associated with said waveguide, said grating structure being arranged to an incident surface of said substrate, said incident surface being intended to receive an incident light beam provided by at least one light source, said incident light beam having an incident angle, defined relative to the normal of said waveguide, said grating structure comprising at least one elementary structure comprising at least a first-type grating structure and at least a second-type grating structure, said first type and second type grating structure having different grating periods and/or different grating orientations. In other words, said first type and second type grating structures present different effective grating periods, as it will detailed after.

The waveguide of the guided mode resonance device is arranged to transfer light from the first-type grating structures to the second-type grating structure and also to transfer light from the second-type grating structures to the first-type grating structure. The waveguide is made of a material of a refractive index at least 0.05 higher than the refractive index of the material adjacent to the side of the waveguide opposite to the incident surface. This allows using a wide variety of materials for the substrate, the waveguide and any possible intermediate layer between the substrate and the waveguide.

The first-type grating structures is arranged to incouple into said waveguide a first portion of said incident light beam and the second-type grating structure is arranged to incouple into said waveguide a second portion of said incident light beam. Also, the first-type grating structure is arranged to couple out, of said waveguide, an outcoupled part of said second portion of said incident light beam, said outcoupled part defining a first light beam and second-type grating structure is arranged to couple out, of said waveguide, an outcoupled part of said first portion of said incident light beam, said outcoupled part defining a second light beam. Said first light beam has a different spectral distribution than said second light beam. By this arrangement at least two light beams may be coupled out of the waveguide of the guided mode resonance device. Such an arrangement may be used in a variety of optical applications wherein an incident light beam having a broad spectral distribution, must be split into two separate beams having a different spectral distribution and wherein the colors of the two beams should be vivid and wherein color contrast between the two said beams must be high. The guided mode resonance device of the invention allows also to have very low levels of stray light due to multiple internal reflections, allowing to improve further the quality and contrast of the colors of the two said beams.

The first light beam and the second light beam produced by the guided mode resonance device have each an outcoupling angle, defined relative to the normal to the waveguide, so that said first and second light beams are not symmetric, relative to the normal to the waveguide, to said incident light beam. This arrangement, also called a non-specular arrangement, allows reducing interference and stray light effects, which are typical for specular beams, wherein a reflected beam is substantially symmetric, relative to the normal of a metallic or multilayer dielectric surface, device, with an incident light beam. Therefore, the guided mode resonance device will have superior optical properties compared to other optical devices that split a light beam in at least two parts having a different spectral distribution. Also, the device is simple to produce so also cheap. The first and second outcoupled light beams are in a general case dispersive, having different out-coupling angles for different wavelengths. The first light beams and second light beams can each contain different spectral bands corresponding to different in and out-coupling resonances of the gratings. For these reasons, an out-coupled first light beam or a second light beam may contain different wavelength bands that are out-coupled at different angles. The angular color distribution in said first light beam and said second light beam may be continuous or discontinuous According to an embodiment, the guided mode resonance device may comprise at least one elementary structure comprising two first-type grating structures, and one second-type grating structure which may be arranged in between said two first-type grating structures. Such an arrangement allows to extend the optical design flexibility and allows generating up to three different outcoupled light beams, each having a different spectral distribution.

The material of said waveguide the guided mode resonance device may be chosen from a group comprising TiO2, or HfO2, or Ta2O5, or ZrO2, or AlN, or Al2O3, or ZnO, or SiO2, or Si3N4, or MgF2, or CaF2, or MgO, or combinations thereof. This wide choice of materials allows using the guided mode resonance device for a wide range of applications, each needing a specific spectral distribution of said outcoupled beams.

In a preferred embodiment, the guided mode resonance device said grating structures are arranged on the surface of said substrate facing said incident light beam. This allows obtaining a good color contrast between the outcoupled beams.

In an embodiment an intermediate layer is arranged between said substrate and said grating structure. The arrangement of said intermediate layer allows to extend the design possibilities, and may also be used to improve the refractive index matching, between said waveguide and said substrate of the guided mode resonance device.

Each of said first light beam and said second light beams may be a visible light beam, or may be a near-infrared light beam, or may be an infrared light beam or may be an UV light beam or its spectral distribution may cover parts of these different ranges. The first and second light beam may be in the same wavelength range or in another wavelength range. The possibility to design and arrange the grating structures and the waveguide of the guided mode resonance device for different wavelengths allows widening considerably the number of possible applications in the UV, visible and infrared range or in a combination of these ranges.

The spectral bandwidths of said first light beam and said second light beam are smaller than 250 nm, preferably smaller than 100 nm, and the central wavelengths of said bandwidths differ by more than 10 nm, preferably 30 nm, more preferably 50 nm. Large bandwidths allow using the device for applications wherein the eye observes the outcoupled light beams of the guided mode resonance device or when a high outcoupled power intensity is required. The adaptation of the device such that the outcoupled beams have small bandwidths, allows to use the device for specific applications such as in the field of gas and/or bio-chemical sensing applications.

In an embodiment said first light beam and said second light beam have an outcoupling angle differing by more than 10° than said incident angle. In a variant, the aperture of said first beam and/or said second beam is smaller than 10°, preferably smaller than 5°, more preferably smaller than 2°. The possibility to design and arrange the first and second type gratings so that different outcoupled angles have each the same or different apertures allows to improve further the design capabilities and so the possible field of applications.

In an embodiment the guided mode resonance device may comprise an array of said elementary structures. Said array may comprise at least two elementary structures, each elementary structure of said array being arranged to cooperate, i.e. by exchanging light, with adjacent said elementary structures. Adapting different elementary structures in an array allows further expanding the design variants of the device. One of the main advantages of using the said elementary structures in arrays is to improve the surface coverage and the outcoupled optical power density, per unit of surface. This in turns can translate in higher visibility or sensitivity of the observed outcoupled light. In designing an array, it is especially interesting to have each said grating structure incoupling and outcoupling light to/from its neighbors grating structures to maximize the outcoupled optical power density.

In another embodiment at least a third-type grating structure is arranged in said array, and said third type grating structure is positioned adjacent to either said first-type grating structure or said second-type grating structure. Said third-type grating structure is arranged to incouple a third portion of said incident light beam into said waveguide, said third portion is transferred by said waveguide to said first-type grating structure or to said second-type of grating structure. Said third-type grating structure is further arranged to outcouple a part of said first portion of said incident light, or a part of said second portion of said incident light, out of the waveguide, said outcoupled part defining a third light beam. The third light beam has optical characteristics similar to the optical characteristics of said first light beam or said second light beam. Arranging a third-type grating in the elementary grating structure allows enhancing the design possibilities of the device.

In an embodiment an array of at least two elementary structures comprising at least a third-type grating is arranged to the guided mode resonating device, and each elementary structure of said array is arranged to cooperate, by exchanging light, with adjacent said elementary structures.

In a further embodiment elementary structures may be arranged in a two dimensional array. Said array may comprise parallel rows of elementary structures, or may comprise non-parallel rows of elementary structures. Arranging said elementary structures in an array allows expanding further the design flexibility of the guided mode resonance device and also the possible range of applications.

In another embodiment said elementary structures may comprise at least one further optical structure. Said further optical structures may be a grating structure or may be a microlens array. In a variant, further optical structures are arranged adjacent to said elementary structures. Said further optical structures may be grating structures or may be a microlens array. Incorporating said further optical structures in the guided mode resonance device allows to improve the functionality of the device, for example by integrating an optical structure allowing to verify stray light and/or the guided total light intensity and so enabling to check the functionality of the device. In optical security applications, other optical security elements may be incorporated more or less closely with the said elementary structures. Such optical security elements may be holograms, zero order devices, moiré, microlenses, reflective or scattering surfaces, optical couplers, optically variable inks, non-variable inks or a combination of them.

In an embodiment a coating layer is arranged to a side of said waveguide facing said incident light beam, said coating layer being arranged at least on a portion of said waveguide. Adapting a coating to the device may be useful to protect the device in some applications. As an example, this coating may be designed as an optical cladding providing mechanical and environmental robustness to said elementary structures.

The invention relates also to a gas sensing device comprising a guided mode resonance device according to the invention, and wherein said guided mode resonance device is arranged so that the spectral distribution of said first light beam and/or said second light beam is modified by the change of the permittivity of at least one of the materials of the substrate, the waveguide, the grating or of their surrounding layers such as the said intermediate layers or the said coating. This change of permittivity may impact the refractive index or the absorption coefficient of at least one of these materials due to a change of the concentration of said gas being in contact with said elementary structure. A device based on the effect of the change of the refractive index by a varying gas concentration allows making a simple, cheap and rapid gas sensing device. The combination of different said elementary structures or different said arrays of elementary structure functionalized with different materials allows engineering various gas sensitivities, selectivities and kinetics to detect and monitor the presence of various mixtures of gases.

In an embodiment the gas sensing device comprises an optical system arranged to redirect and/or change the divergence of said first light beam and/or said second light beam and/or said incident light beam. The gas sensing device may comprise at least one photodetector to measure the intensity of at least one of said first or said second light beam. A gas sensing device based on a guided mode resonance device according to the invention allows realizing a miniaturized and passive gas sensing device and allows also, by the instantaneous detection of the change of the spectral distribution of said first and second light beams a quick detection of a gas.

The object of the invention is also obtained by a method for gas sensing comprising the steps of:

providing the gas sensing device as previously mentioned,
positioning a light source to the side of said grating structures of the gas sensing device or using a light source from the environment of use,
introducing a gas, or changing the concentration of a gas in the immediate environment of the guided mode resonance device, said gas being arranged to contact said grating structures and said waveguide,
observing by the eye or detecting with at least one photodetector the change of spectral distribution of said first light beam and said second light beam.

The method to detect gas according to the invention allows providing a simple, cheap and quick way to detect particular gases. An example of such a gas is ammonium. The method to detect gas according to the invention may use a very basic optical system or may be performed without additional optical components, allowing detecting the gas by simply observing the colors of said outcoupled beams by the eye.

The invention also relates to a bio-chemical sensing device of a bio-chemical substance comprising a guided mode resonance device according to the invention, and comprises a bio-chemical layer designed for reacting with said bio-chemical substance. Said bio-chemical layer is arranged in contact with said waveguide and/or said grating structure, and said bio-chemical sensing device is arranged so that the spectral distribution of said first light beam and/or said second light beam is modified by the reaction of said bio-chemical substance with said bio-chemical layer. A bio-chemical sensing device according to the invention allows making a simple and cheap device which may be dispensable. It is obvious to the man skilled in the art that the transduction mechanisms disclosed for gas sensing, converting a change of chemical concentration to a change in an optical behavior can be engineered and optimized, with another specific functionalization, to detect other chemical species.

In an embodiment, the bio-chemical sensing device comprises a fixing layer, said fixing layer being arranged to incorporate said bio-chemical layer.

In an embodiment, the fixing layer of the bio-chemical sensing device is a polymer layer, a porous layer or a gel layer. The adaptation of a said fixing layer to the device is designed to provide a specific chemical bonding and/or a physisorption and/or a chemical reaction that will create a change of the permittivity in the optical proximity to the said waveguide and/or said grating structure.

The bio-chemical sensing device of the invention may comprise an optical system arranged to redirect and/or change the divergence of said first light beam and/or said second light beam and/or said incident light beam.

The device of the invention may also comprise at least one photodetector. Said optical system and photodetector may be similar to the ones implemented in the gas sensing device of the invention. Adapting an optical system to said bio-chemical sensor allows designing a sensor platform adapted to a wide variety of possible configurations such as point of care diagnostics.

The object of the invention is also obtained by a method for sensing of a bio-chemical substance comprising the steps of:
providing a bio-chemical sensing device according to the invention,
positioning a light source to the side of said grating structures of the guided mode resonance device or using an available light source from the environment in which the bio-chemical sensing device is used, said light source may be sunlight or an artificial light source,
applying said bio-chemical substance so that it is diffused, transported or migrated to come in contact with said bio-chemical layer
provoking a reaction, for example a bonding reaction and/or an adsorption reaction between said substance and said bio-chemical layer,
observing by the eye or detecting with a photo detector the change of spectral distribution of said first light beam and said second light beam.

The method to detect bio-chemical substances according to the invention allows providing a simple, cheap and quick way to detect particular bio-chemical substances. This can be used for example in bio-monitoring or in diagnostics. An example of such bio-chemical substances are antibodies. The method to detect bio-chemical substances according to the invention may use a very basic optical system or may be performed without additional optical components, allowing the detection of one or more bio-chemical substances by simply observing the colors of said outcoupled beams by the eye.

The invention relates also to a security document and/or a document of value including a said guided mode resonance device as above-mentioned. The color brightness of the outcoupled at least first light beam and second light beam by the guided mode resonance device allows realizing visible security signs, which highly contrasted colors, with optically variable effects such as change of intensity and color with variable angles of illumination and/or observation.

BRIEF DESCRIPTION OF THE DRAWINGS

The above described objects and advantages of the present invention will become more readily apparent to those ordinarily skilled in the art after reviewing the following detailed descriptions and accompanying drawings, in which.

DETAILED DESCRIPTION

Resonating waveguide gratings (RWG), also called leaky mode filters or also guided-mode resonance filters or guided-mode resonance devices are well described in the literature. The functional principle of these devices is based on a resonance phenomenon that may occur in waveguide grating structures. Resonant waveguide gratings consist of a combination of a subwavelength grating and a thin film waveguide. The subwavelength grating acts as an incoupling grating for the waveguide. A resonance occurs when a portion of the incident light, diffracted by the grating, matches a mode of the waveguide. As most of the spectrum of the incident light on the grating does not couple into the waveguide, strong spectral changes may be observed in reflection and/or transmission. The resonance effects, their theoretical explanation and their applications have been extensively described in the past and will not be further commented here. Relevant information on this subject may be found in the following references:

Hessel and Oliner: Appl. Optics, vol. 4, pp. 1275-1297, 1965);

R. F. Delmdahl et al., <<Spectral resolution analysis of resonant grating waveguides>>, Mat. Wiss.u. Werkstofftechc., 38, nr. 3, 2007;

D. Rosenblatt et al., "Resonating grating waveguide structures", IEEE J. Quantum Electron., vol. 33, nr. 11. pp. 2038-2059, 1997;

A. Sharon et al.: "Resonating grating-wavegudie structures for visible and near-infrared radiation:", J. Opt. Soc. Am., vol. 14, nr. 11, pp. 2985-2993, 1997.

Figure 1:
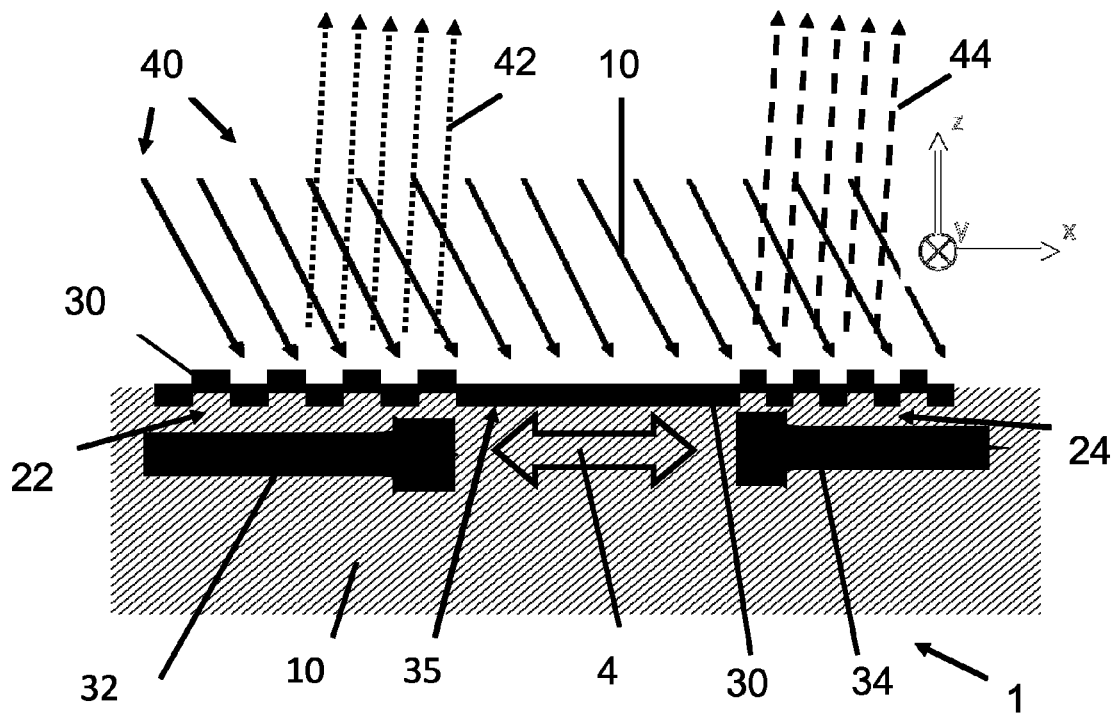
FIG. 1 illustrates a cross section of a guided mode resonance device.

A preferred embodiment of a guided mode resonance device 1 of the invention is illustrated in FIG. 1. Said preferred embodiment configuration comprises the following basic configuration:

a substrate 10, comprising an incident light surface, adapted to receive a light beam 40, said incident light surface being also defined as the incident surface, also defined as the substrate plane, an elementary grating structure, arranged on said substrate 10, adapted to receive a light beam and comprising at least two different grating structures having two different grating periods, said two different grating structures being defined as a first-type grating structure 22 and a second-type grating structure 24, a waveguide layer 30, defined also as waveguide 30, arranged on said elementary grating structure 2, said waveguide 30 being arranged to guide at least a portion of light coupled into said waveguide 30 by said two different grating structures.

For clarity, x, y and z directions are defined as following: the z direction is the direction of the normal direction, defined as perpendicular to said incident surface. The x direction is defined as being substantially the direction of the travel 4, also defined as guidance, of the light coupled into said waveguide 30 layer and the y-direction is defined in the plane of the waveguide 30, normal to the x-direction. The y direction corresponds substantially to the direction of the grating lines, defined also as grating patterns, as further defined. As the waveguide thickness, defined in the z-direction is very small, the x-y plane defines substantially the substrate plane. Said x, y, z directions are shown in FIG. 1.

The incident light beam 40, also defined as the incident light 40, may be visible light, near-infra-red light, infrared light or UV light or a combination of these wavelength ranges. The wording "visible" as used herein means light having wavelengths between 400 nm and 680 nm, "near-infrared" means light having wavelengths between 680 nm and 2 μm, "infra-red" means light having wavelengths greater than 2 μm, and "UV" light means light having wavelengths lower than 400 nm.

The substrate 10 is preferably a substantial homogeneous layer and is preferably a glass substrate 10 or more preferably a polymer substrate 10. Eventually the substrate 10 can contain additional layers such as but not limited to adhesion layers, barrier film layers or protection coatings. The substrate 10 may be a rigid substrate 10 or may be a flexible foil substrate 10. The thickness of the substrate 10 may be between 5 microns and 20 mm, preferable between 0.5 mm and 3 mm. Said substrate 10 may not be transparent to at least a portion of said incident light beam 40. The refractive index of the substrate 10 has a value at least 0.05 lower than the refractive index of the waveguide 30.

In a preferred embodiment said grating structures are arranged directly on said incident surface of said substrate 10. Said grating structures may be realized preferably, but not limited to, by embossing techniques or UV casting techniques or dry reactive ion etching (DRIE)-reactive etching techniques, resulting in the structuring of said incident light surface of the substrate 10. Said first-type grating structure 22 and said second-type grating structure 24 comprise grating patterns, defined also as grating elements, arranged to couple light incident on said grating structures. Said grating elements may be substantially binary and/or sinusoidal and/or cycloid grating elements. Said first-type grating structure 22 and said second-type grating structure 24 are different types of grating structures having different effective grating periods. The effective period can be defined as the period in the x-direction. The following parameters may also be adapted for the different grating types:

the grating depth (d) defined between the highest and the lowest point of the grating pattern, said grating depth having a subwavelength dimension, the width (w) of the grating elements, having a subwavelength dimension, the feature size, defined as the ratio d/w between the depth and the width of the grating elements, the profile of the grating elements, defined in the x-z plane defined by the incident light beam 40 and the diffracted light beam by said grating elements the shape of the patterns of the gratings in the x-y plane of the surface of the substrate 10, the orientation of the grating in the x-y plane.

In the present application two similar gratings that have a different orientation in the x-y plane relative to the waveguide 30 are also defined as different type of gratings, as their effective period relative to the propagation direction (x-direction) in from the waveguide 30 is different. Said first type grating structure and said second type grating structure have necessarily different grating effective periods along the propagation direction of the light beam inside the said-waveguide 30. This can be realized by having the two grating types having different periods or having substantially the same period but having different grating orientation in the x-y plane, relative to the said x direction, being substantially the direction of the travel, also defined as guidance, of the light into said waveguide 30 layer. This condition translates into the first light beam 42 and the second light beam 44 being outcoupled at angles not symmetric, relative to the normal or z-direction, to the incident light 40 beam or not parallel to the said incident light 40 beam.

As an example, in visible light applications, the grating depth of the gratings is between 5 nm and 300 nm, preferably between 10 nm and 60 nm. The grating depth and the grating period have subwavelength dimensions chosen such that moderate to high-coupling efficiency is achieved for the wavelength range to be incoupled into the waveguide 30. Moderate coupling efficiency allows the light 4 transported into the said resonant waveguide grating 22 not to be outcoupled too efficiently and to propagate further away into the said waveguide 30. Further transport distance in the region of the resonant waveguide grating 22 enables a stronger chromatic or wavelength filtering of the light coupled into the waveguide 30.

Said first-type grating structure 22 and said second-type grating structure 24 may each have different dimensions, defined in the x-direction and/or the y-direction as detailed above.

Said first-type grating structure 22 and said second-type grating structure 24 may comprise a coating, intended to improve the diffraction efficiency and the incoupling of light into a waveguide 30. Said coating may be a multilayer coating.

One can refer to the patent application PCT/EP2013/065631 filed by the applicant to obtain details regarding the method of realization of said first-type 22 and/or said second-type grating structure 24. Said first-type grating structure 22 and said second-type grating structure 24 realization methods are not limited to the ones disclosed in PCT/EP2013/065631. It should be noted that the structures discussed in the patent application PCT/EP2013/065631 are optimized for coupling into a massively multi-mode waveguide, whereas in this document monomode waveguides, bi-mode, tri-mode waveguides, are of core interest. Multi-mode waveguides with more than 3 modes are also possible.

Said waveguide layer 30, also defined as a waveguide 30, is preferably a waveguide coating deposited on said grating elements of said first-type grating structure 22 and said second-type grating structure 24 and may also be deposited or arranged on a portion of the surface of the substrate 10 that separates said first-type and said second-type grating structure 24. Said first-type 22 and second-type grating structure 24 may be adjacent to each other. Said waveguide 30 layer is arranged on said first-type grating structure 22 and said second-type grating structure 24 so that a portion of the incident light 40 on said first-type grating structure 22 and a second-type grating structure 24 is coupled into the waveguide 30 of the guided mode resonance device 1. The material of said waveguide 30 may be chosen from a group comprising TiO2, or HfO2, or Ta2O5, or ZrO2, or AlN, or Al2O3, or ZnO, or SiO2, or intrinsic Si, or doped Si, or Si3N4, or MgF2, or CaF2, or MgO, or combinations thereof. Said waveguide layer 30 is a layer having substantially the same width, defined in the y-direction, as the width of said grating elements, also defined in the y direction. Said waveguide 30 may be larger, in the y direction, than the grating structures and may extend on the whole substrate 10 surface if arrays of said guided mode resonance device 1 are patterned on the substrate 10, as further illustrated in FIG. 9. Said width is typically 10 μm to 100 mm, preferably 50 μm to 1000 μm. The thickness of said waveguide 30, defined in the z-direction, depends on the wavelength of the light to be incoupled in said waveguide 30 is typically, but not limited to, 10 nm to 1000 nm. Said waveguide 30 may have a substantially strip shape. The waveguide 30 may be a straight waveguide 30 or may be curved waveguide 30, as defined in the x-y plane. The waveguide 30 may have a more complex shape, defined in the x-y plane, such as an L-shape. Waveguides 30 may be arranged as crossing waveguides 30, in which case the waveguide arrangement has a substantially X-shape, with each waveguide 30 comprising at least a first-type and a second-type grating structure 24.

Said grating parameters of said first-type grating structure 22 and said second-type grating structure 24 are advantageously chosen so that said first-type grating structure 22 and said second-type grating structure 24 couple each into said waveguide 30 a different portion of said incident light 40 beam. Said first-type grating structure 22 incouples a first portion 32 of the incident light 40 into said waveguide 30 and said second-type grating structure 24 incouples a second portion 34 of the incident light 40 into said waveguide 30. Said first portion 32 and said second portion 34 may have substantially the same intensity, but not necessarily so. In some applications the guided light power of said first portion 32 and said second portion 34 may be different by a factor of 2 or even more, for example a factor 10. The first-type grating structure 22 is arranged to couple out, of said waveguide 30, an outcoupled part of said second portion 34 of said incident light 40 beam, said outcoupled part defining a first light beam 42 and second-type grating structure 24 is arranged to couple out, of said waveguide 30, an outcoupled part of said first portion 32 of said incident light beam 40, said outcoupled part defining a second light beam 44. In the present document the term communication is hereafter defined as the outcoupling out of the waveguide 30, by a grating type, of a part of the light beam incoupled in another location of the waveguide 30 by another type of grating. The term communication includes also the case wherein each of two different grating types is an outcoupler of light incoupled by the other of said two different grating types. Light power densities of said first and second beam is preferable substantially the same, but they may also be different. Said first light beam 42 has a different spectral distribution than said second light beam 44.

Said first light beam 42 and said second light beam 44 have each an outcoupling angle preferably differing by more than 10° than said incident angle. In a variant, the aperture of said first beam 42 and/or said second beam is smaller than 10°, preferably smaller than 5°, more preferably smaller than 2°.

The first light beam 42 and second light beam 44 will propagate out of the said guided mode resonant device at angles being dependent of the incident beam angle and of the wavelength range considered. Said first portion 32 and second portion 34 are determined, for a specific wavelength range, by choosing and optimizing the grating parameters of said first-type grating structure 22, of said second-type grating structure 24 and the waveguide 30 material and thickness. Said choice and optimization is performed in function of the application and the desired light effects realized with the guided mode resonance device 1.

Figure 3:
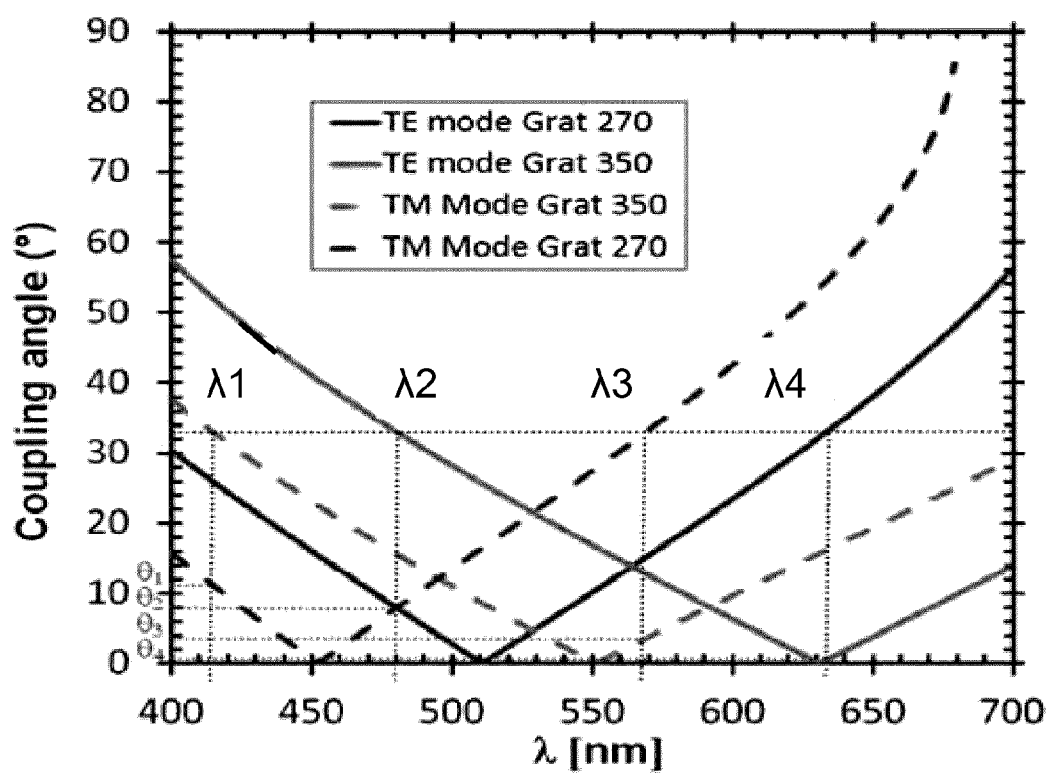
FIG. 3 illustrates a simulation of the guided mode resonance device.

FIG. 3 illustrates a simulation result with the resonance locations for a guided mode resonance device 1 having the following parameters:
  grating period of the first-type grating structure: 270 nm;
  grating period of the second-type grating structure: 350 nm;
  grating depth: 40 nm;
  waveguide thickness (in z): 100 nm;
  waveguide refractive index: 2.4;
  refractive index of the substrate 10: 1.5;

refractive index of the gas (air) at the incident light 40 side of the grating structures: 1;

incoupling angle from substrate normal: 33°.

FIG. 3 shows the locations of coupling resonances of the structure described above, for a grating of period of 270 nm and 350 nm with an incidence of 33°.

Light is in-coupled in the waveguide 30 by the first-type grating 22 around the central wavelength as follows, and is out-coupled by the second type grating 24 around the following angle:

for TM −1st diffractive order at 450 nm the output angle is 11°;

type for TE −1st diffractive order at 515 nm the output angle is 8°.

Light is in-coupled in the waveguide 30 by the second type grating 24 around the central wavelength as follows, and is out-coupled by the first type grating 22 around the following angle:

for TM +1st diffractive order at 565 nm the output angle is 4°;

type for TE +1st diffractive order at 635 nm the output angle is 0°.

In this example, the light is in-coupled, from a light source, illuminating with an incident light beam 40 at an angle of 33° the guided mode resonant device 1, at two different wavelengths for each of the first 22 and second 24 type gratings, one resonance occurring for each of the TE and TM polarizations for each type of grating and will propagate to the other grating type. The diffractive order sign, minus for the first type grating 22 and plus for the second type grating 24, allow the in-coupled light beam in the waveguide 30 to propagate in opposite directions. With the first 22 and second 24 grating types correctly arranged on the left or right of each other for a given illumination direction, the propagating modes in the waveguide 30 will reach the opposite grating types and be out-coupled into the first and second light beams. These 4 coupled modes will be outcoupled from the waveguide 30 by the other type of grating at various angles and each having a unique polarization. As an example, the TE −1st diffractive order coupled by the first type grating 22 will be outcoupled by the second type grating 24 around 8° with a spectral bandwidth centered on 515 nm.

Figure 2A:
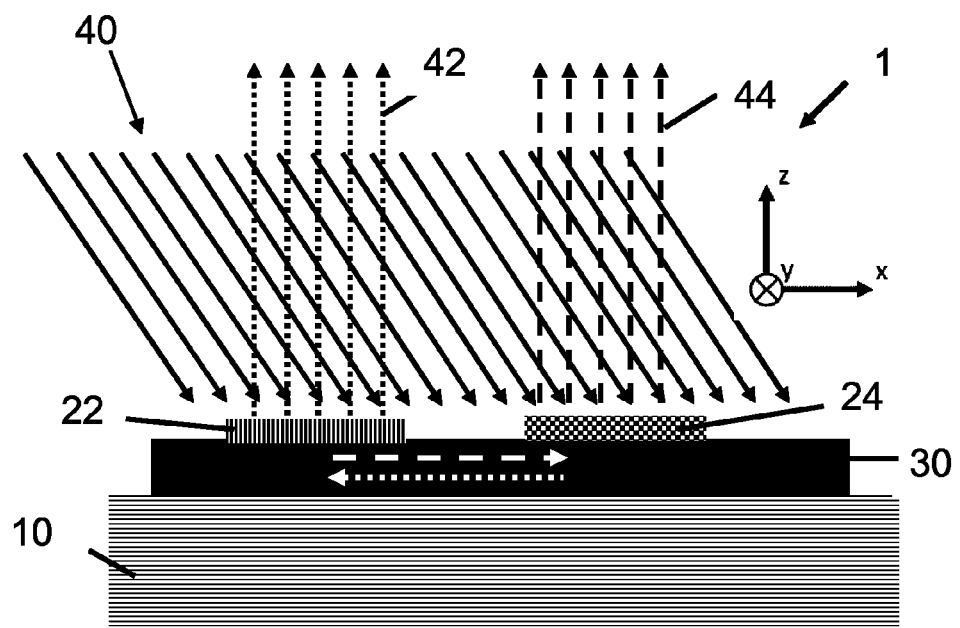
FIG. 2a illustrates an elementary grating structure comprising a first-type grating structure and a second-type grating structure.

Said first-type grating structure 22 and said second-type grating structure 24 may be arranged adjacent to each other or they may be separated, as illustrated in FIG. 2a, by a portion of said waveguide 30, said portion being defined as a separation section 35, said separation section 35 connecting said grating structures. The choice of the length of said separation section 35 depends on the application. In the case of the use of the guided mode resonance device 1 for sensing applications said separation section 35 is chosen as large as possible, allowing to enhance the interaction of the evanescent portion of the wave guided by the waveguide 30 with the direct environment, in contact with said waveguide 30. The length of the separation section 35 is chosen to obtain a compromise between the desired sensitivity and the optical power density per surface area of said first beam and said second beam, impacted by the light loss along the waveguide and by the number of elementary grating structures. Said comprise depends on the particular application.

A typical length of said separation section 35 is 5 µm to 5 mm, preferably 20 µm to 0.5 mm. The length of said separation section 35 may be substantially zero, for example in applications for security devices where the outcoupled power density per unit of area is the main desired optical property. In that case said grating structures are arranged substantially adjacent to each other and are linked by a waveguide 30 whose length, in the x direction is substantially the sum of the length of the first-type 22 and second-type grating structure 24, defined in the x direction.

A preferred dimension of said first-type grating structure 22 and said second-type grating structure 24, in the direction of the propagated light, which is substantially the x-direction, is between 3 µm and 2 mm, preferably between 20 µm and 0.5 mm and depend of the wavelength range considered. The cross section of said incident light beam 40, defined perpendicular to the propagation direction of said incident light beam 40, may cover completely or partially, at said incident surface, of said guided mode resonance device 1, said first-type grating structure 22 and said second-type grating structure 24. The incident light 40 beam may be a single light beam covering at least partially said first-type grating structure 22 and said second-type grating structure 24. The incident light 40 beam may comprise at least a first incident light beam part and a second incident light beam part, each of said incident light beam parts illuminating at least partially said first-type 22 or said second-type grating structures 24.

The diameter of the cross section of the incident light beam 40 depends on the specific configuration of the guided mode resonance device 1 and is typically 0.1 mm to 30 mm, preferably 10 mm to 200 mm. The incident light 40 beam may be provided by a substantially collimated light source or may be provided by a diffuse light source. The light source may comprise several light sources.

A mask, comprising an opaque layer and at least one aperture, intended to block at least partially the incident light 40 for a part of the spectrum of the incident light 40 beam, may be arranged to the of the guided mode resonance device 1. Said mask may comprise at least an opening facing said first-type grating structure 22 and said second-type grating structure 24 and/or said waveguide 30. Said mask may be combined with an optical filter. Said mask may be arranged to reduce at least a fraction of stray light. An optical filter may be arranged on said guided mode resonance device 1. Said optical filter may be combined with said mask.

Figure 4A:
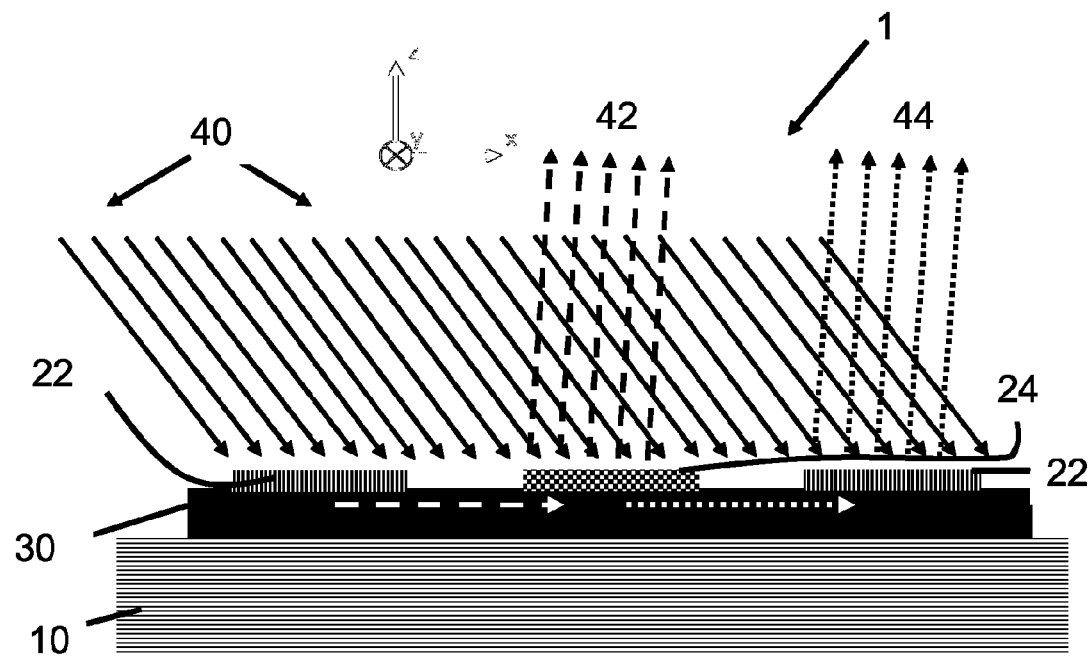
FIG. 4 a, b, c illustrate different embodiments of an elementary grating structure comprising at least two first-type grating structures.

In another embodiment, said elementary grating structure 2 may comprise at least two-first type grating structures, as illustrated in FIG. 4a, b, c. In a preferred variant illustrated in FIG. 4 a, b said second-type grating structure 24 is arranged between said two first-type grating structures 22. In said preferred variant of FIG. 4a, b, a first portion 32 of the incident beam 40 is incoupled by at least one of the first-type grating structure 22 and at least a part of this first portion 32 is outcoupled by said second-type grating structure 24. In said preferred variant a second portion 34 of the incident beam 40 is incoupled by the second-type grating structure 24 and at least a part of this second portion 34 is outcoupled by one of said first-type grating structure 22. In said preferred variant illustrated in FIG. 4a, b, one of said two first-type grating structures 22 is arranged as an outcoupler, while the second of said two first-type grating structures 22 is arranged as an incoupler.

Figure 4B:
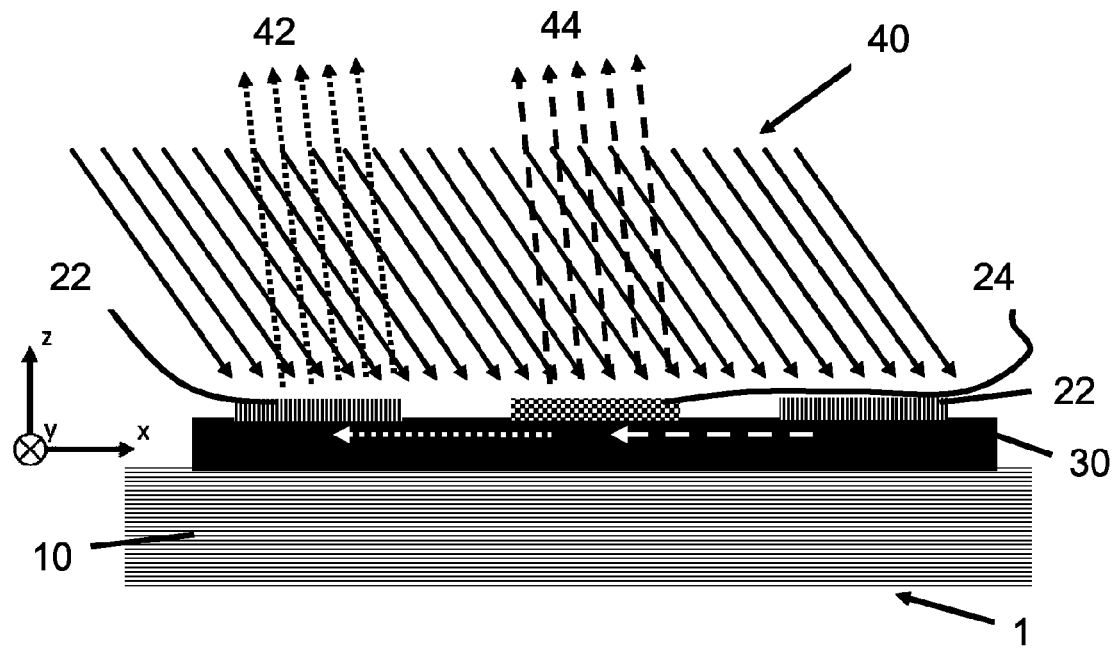
Figure 4C:
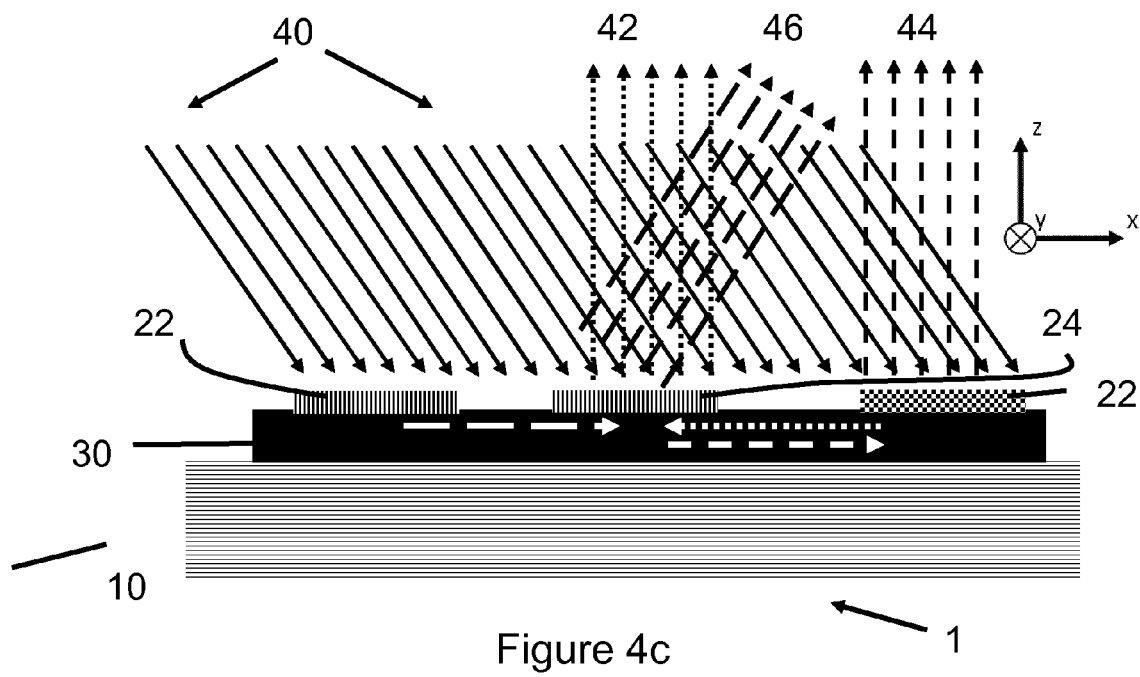

In a variant of the embodiment of FIG. 4a, b one of said two first-type grating structure 22 may be arranged between said second-type grating structure 24 and the second of said first-type grating structure 22, as illustrated in FIG. 4c.

The exchange of light, i.e. the cooperation, between said first-type grating 22 and said second-type grating 24 may be done in the same propagation direction in the waveguide 30, or may be done in two opposite directions as illustrated in the FIG. 4 a, b, c.

Figure 5:
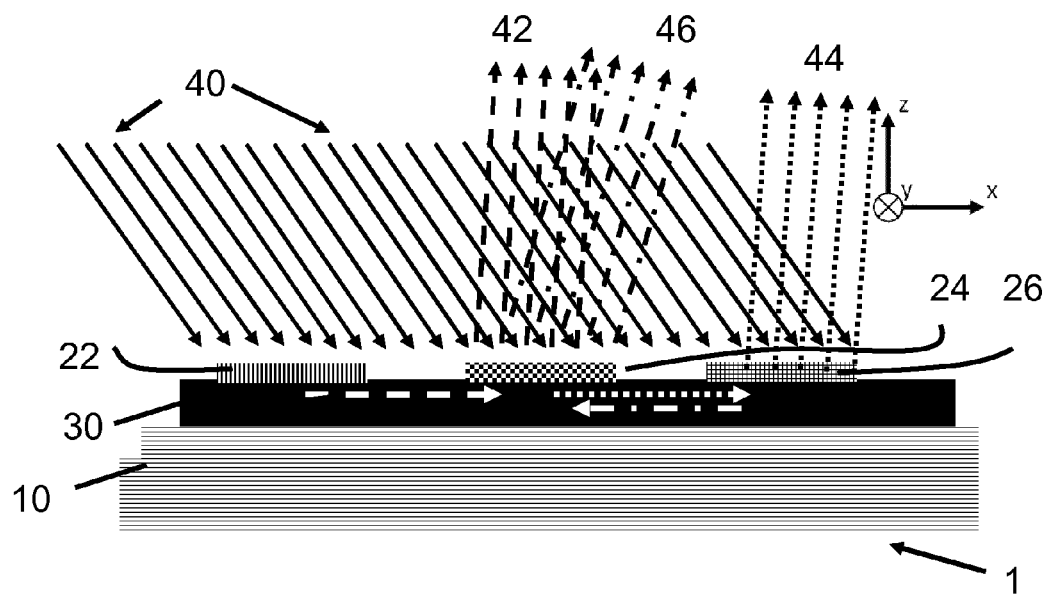
FIG. 5 illustrates another elementary grating structures comprising a first-type grating structure, a second-type grating structure and a third-type grating structure.

In a further embodiment, illustrated in FIG. 5 more than 2 different types of grating structures may be arranged in an array of elementary grating structure. FIG. 5 illustrates an elementary grating structure comprising a first-type 22, a second-type 24 and a third-type 26 grating structure. The guided mode device of FIG. 5 couples out three different light-beams 42, 44, 46. Each of said light beams 42, 44, 46 may have different colors and may each have different beamshapes.

Figure 2B:
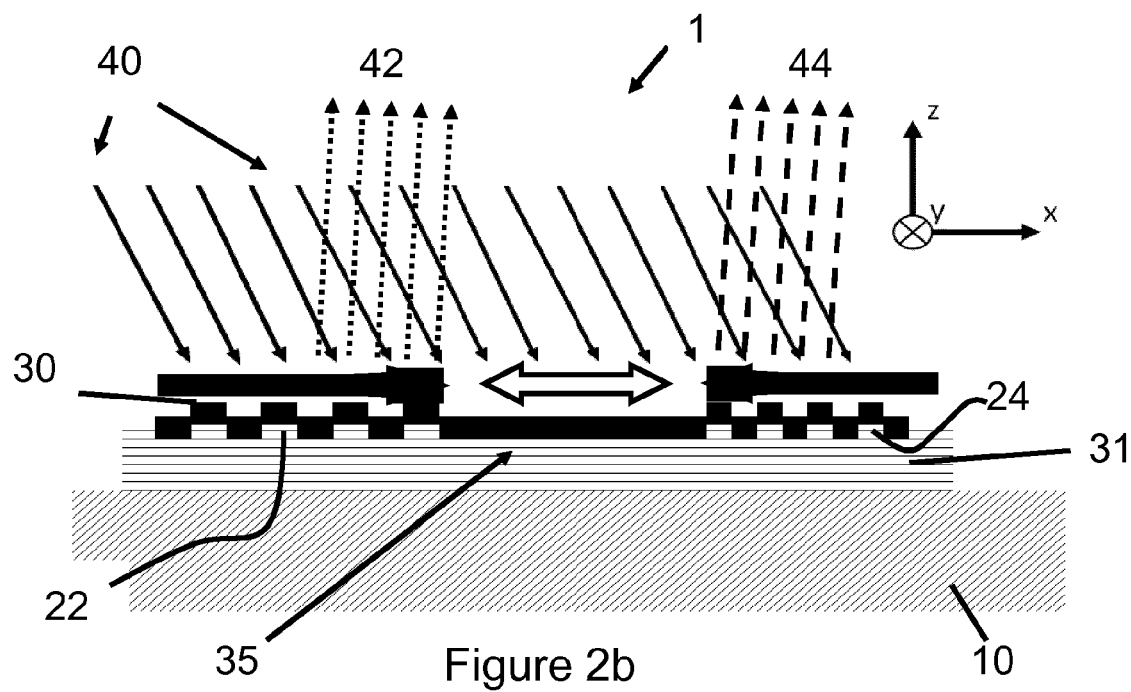
FIG. 2b illustrates an elementary grating structure comprising a an intermediate layer between the waveguide and the substrate.
Figure 6:
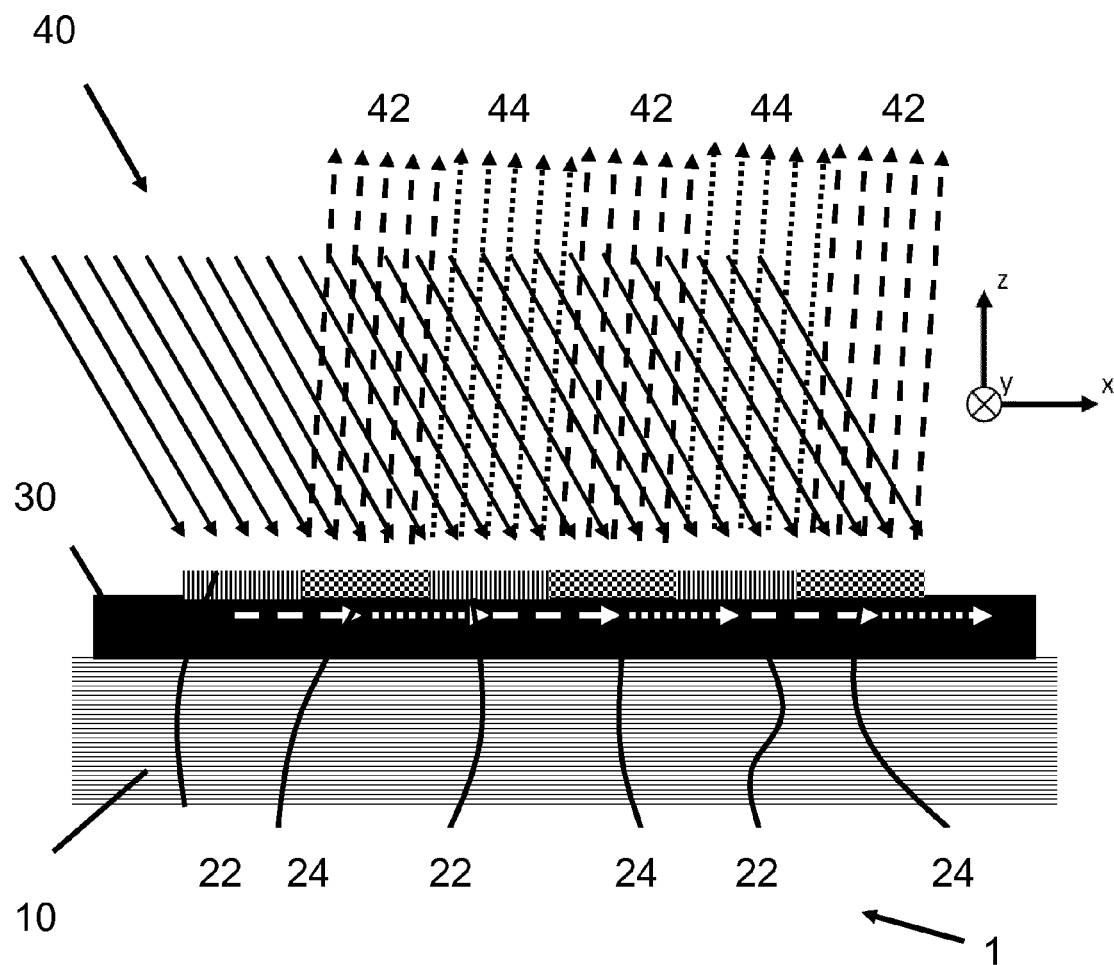
FIG. 6 illustrates a linear array of two cooperating elementary structures comprising each a first-type grating structure and a second-type grating structure.

FIG. 6 illustrates another embodiment wherein at least two elementary grating structures of the embodiment of FIG. 2 are arranged as a linear array in the guided mode resonance device 1.

Figure 7A:
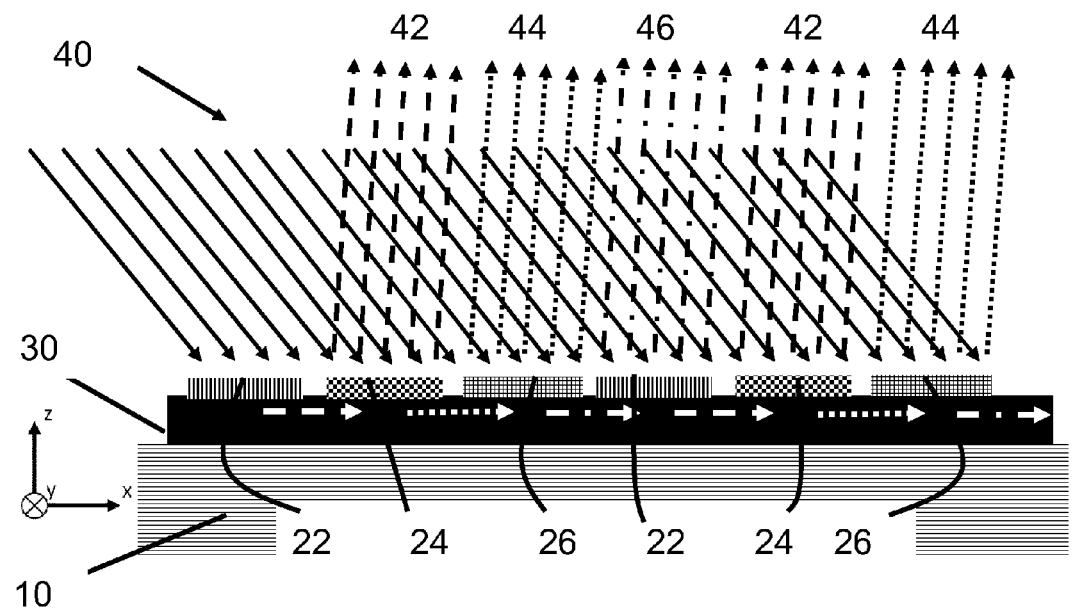
FIG. 7 a, b illustrate a linear array of two cooperating elementary structures comprising each three different types of grating structures.
Figure 7B:
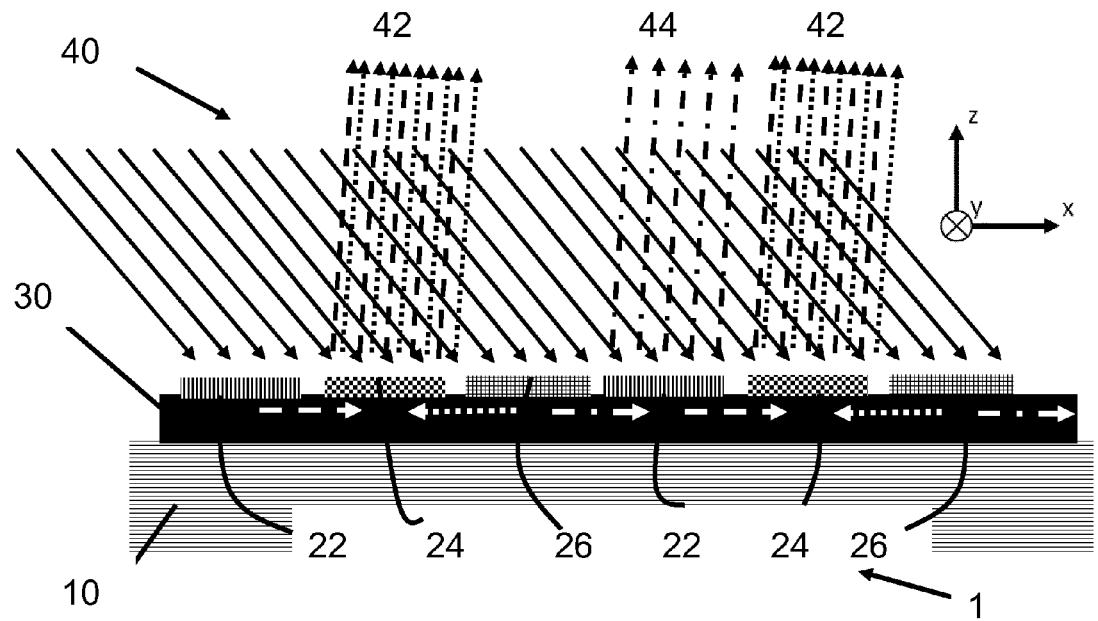

In another embodiment, illustrated in FIG. 7*a, b* at least two elementary grating structures as defined in par. [0066] and shown in FIG. 5, are arranged in a linear array. In the embodiment of FIG. 7*a, b* said at least two grating structures cooperate by exchange of light between two different types of grating structures. Said two different types of grating structures may cooperate between each other inside a single elementary grating structure 2 and /or two different types of grating structures arranged in at least two separate elementary structures may cooperate. The cooperation between two different types of grating structures may be performed even when said grating structures are arranged in two elementary grating structures 2 separated by at least another elementary grating structure 2.

FIG. 8 *a, b, c* illustrate several exemplary arrangements of a linear array of elementary grating structures 2. Not all elementary grating structures of an array need to have the same arrangement of grating structures in each elementary grating structure.

Figure 8A:
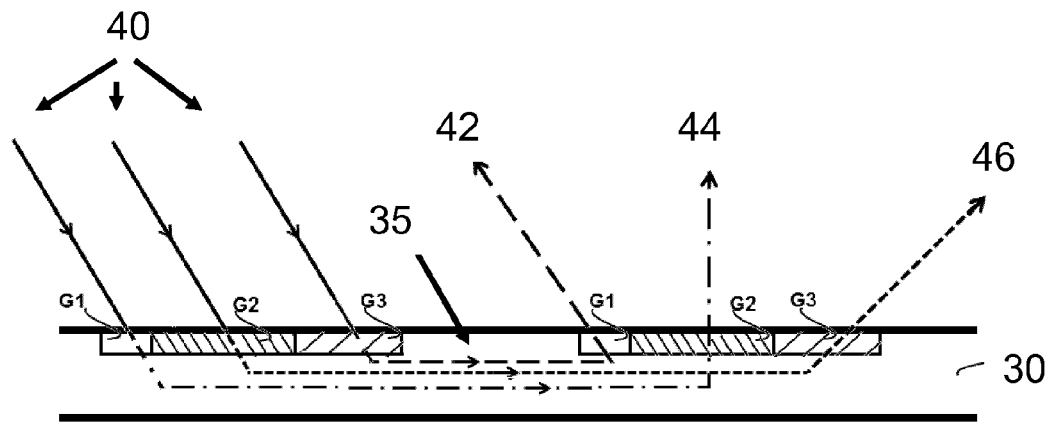
FIG. 8 a, b, c illustrate different configurations of elementary grating structures.
Figure 8B:
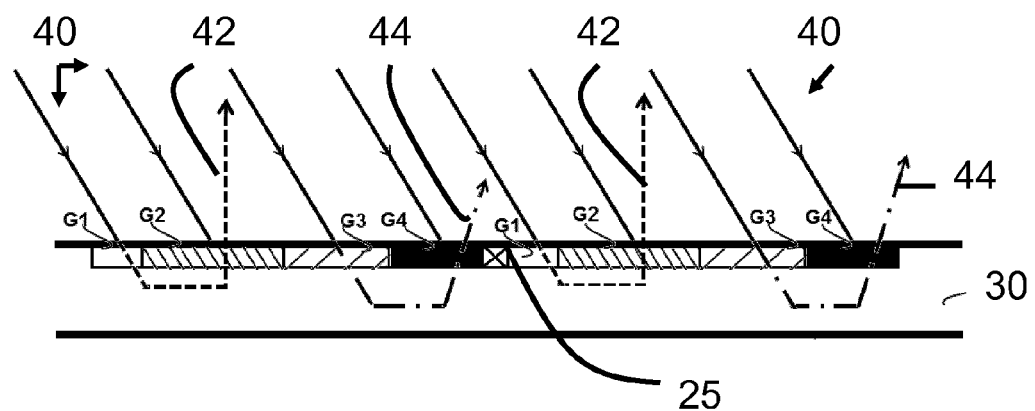
Figure 8C:
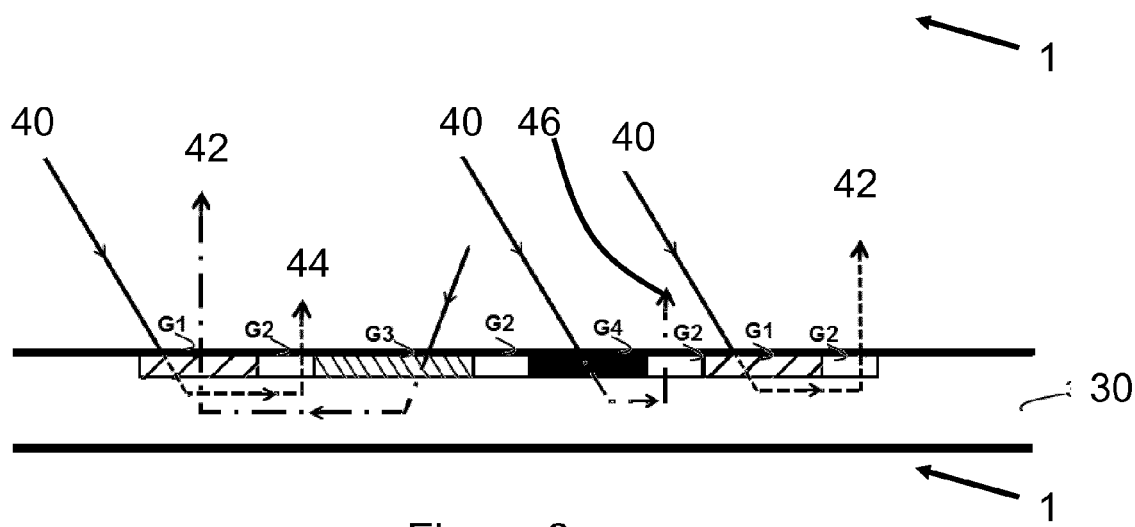

In FIG. 8*a* for example an array is illustrated wherein the two elementary grating structures comprise each a first 22, a second 24 and a third 26 grating structure, respectively defined as G1, G2, G3. In the example of FIG. 8*a*, light incoupled by G1, G2, G3 of the first elementary grating structure is outcoupled respectively by G2, G3, G1 of the second elementary grating structure. FIG. 8*b* and FIG. 8*c* show alternative arrangements of FIG. 8*a*, in which 4 different grating types, defined and illustrated as respectively G1, G2, G3, G4, are arranged as an outcoupler and/or an incoupler. FIG. 8*b*, illustrate several exemplary outcoupled light beams 42, 44, 46. It is obvious that the number of possible combinations of elementary grating structures 2 and the number of types of grating structures arranged in said elementary grating structures in an array of elementary grating structures is not limited to the examples illustrated in FIG. 8.

In another embodiment, a linear array of elementary grating structures may comprise at least an additional grating structure 25 arranged between adjacent elementary grating structures. This is illustrated in FIG. 8*b*. Said additional grating structure may be of another type than the grating structures of said elementary grating structures 2. In a variant, at least a microlens array may be arranged between two adjacent elementary grating structures 2. In another embodiment, an elementary grating structure 2 may comprise at least a microlens array. Said microlens array may be arranged adjacent to an elementary grating structure 2. In a variant, an elementary grating structure 2 may comprise an additional grating structure which does not cooperate, with the other grating structures of said elementary grating structure 2. Said additional grating structure may serve for example to couple light out of the waveguide 30 and determine if stray light is present, allowing to determine if the guided mode resonance device 1 is damaged, or it may serve for intensity referencing purposes. Arranging said additional grating structure and/or said microlens array to the gratings structures and/or the waveguide 30 of the guided mode resonance device 1 may allow to achieve additional functionalities to the guided mode resonance device 1.

In another embodiment of the invention an intermediate layer may be arranged between the substrate 10 and the grating structure. The refractive index of said intermediate layer is higher than 0.05 relative to the refractive index of the waveguide 30 layer. In another embodiment the grating structure may be embedded in said waveguide 30 structure. In a further embodiment the waveguide 30 structure may be arranged on said substrate 10 and said grating structure may be arranged on said waveguide 30. The number of possible arrangements of substrates 10, waveguides 30 and grating structures that allows the realization of a resonating waveguide 30 device is well known to the man skilled in the art and will not be further developed here.

In a further embodiment, a coating layer may be arranged to the incident light 40 side of the guided mode resonance device 1. Said coating may be a protective coating, avoiding possible damage due to the manipulation of the device. Said coating may be a multilayer coating.

Figure 9:
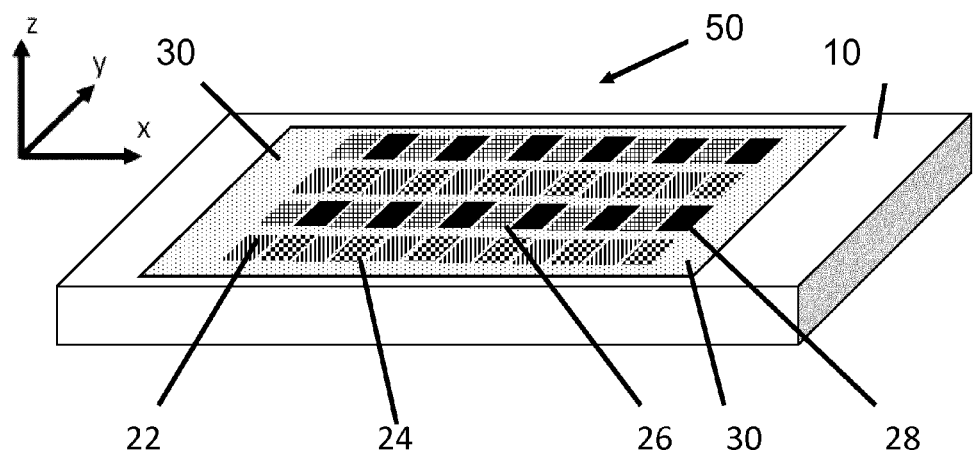
FIG. 9 illustrates a 2D array of elementary grating structures.

In an embodiment, elementary grating structures may be arranged in a 2D array, as illustrated in FIG. 9. All different arrangements of an array elementary grating structures as described are possible in said 2D array. Special optical arrangements may allow the mixing of out-coupled light beams from one row of said 2D array to another and from one column to another, in order to combine different first 42 and second light beams 44 into more complex out-coupled beams. In an embodiment said 2D array may comprise additional grating structures. 2D arrangements of elementary grating structure 2*s* are specifically useful in the field of security device 130 as further explained.

In particular situations, according to the invention, the guided mode resonance device 1 may be arranged to cope with the presence of at least two light sources, at least one light source being positioned to each side of the guided mode resonance device 1.

The fabrication of guided mode resonance devices 1 according to the invention is easy, by for example roll-to-roll processes. On the other hand, the technology required to design and originate them is quite complex and expensive which makes the devices particularly interesting for anti-counterfeiting and security applications.

Figure 10:
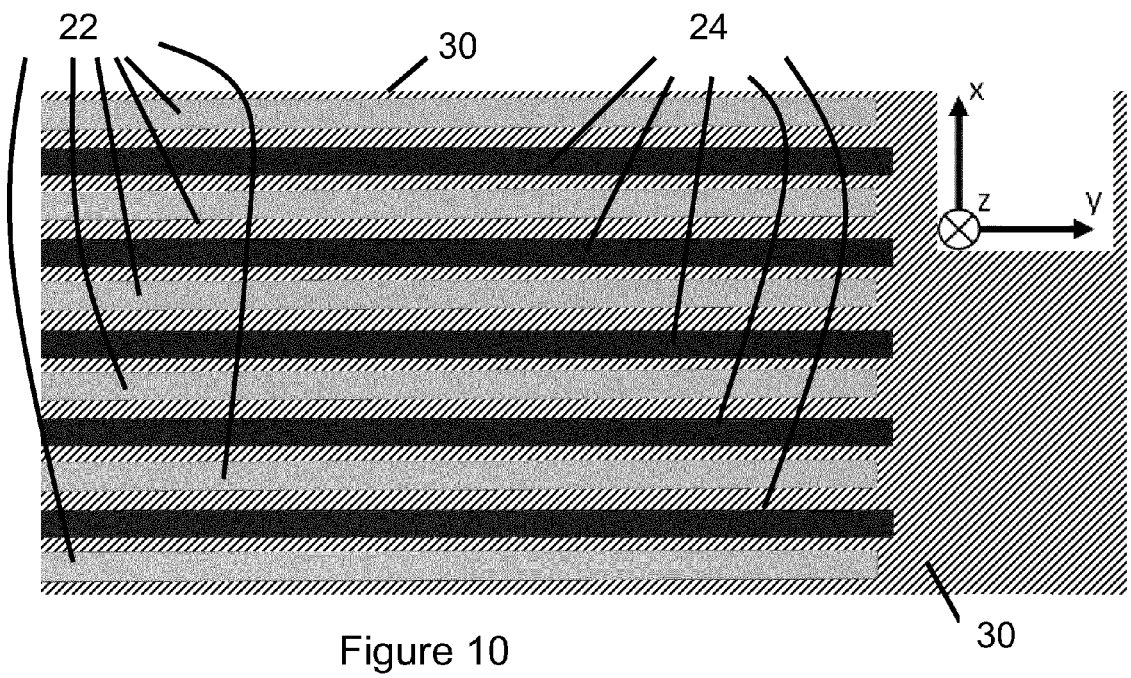
FIG. 10 illustrates a top view of a guide mode resonance device comprising a linear array of elementary grating structures.

FIG. 10 shows a typical realization of an exemplary guided mode resonance device 1 comprising a linear array of first-type gratings and second-type gratings connected by a continuous waveguide 30 and communicating between each other types.

The number and variety of possible applications of the guided mode resonance device 1 may be quite broad. For instance, the device may be implemented in a gas sensing device, a bio-chemical sensor or in security detection systems and devices as outlined further. The guided mode resonance device 1 may also be used as decoration elements, as elements in photovoltaic cells. Devices or systems in which guided mode resonance devices 1 are arranged may have a typical dimension in the mm to cm range but in some applications, typical dimensions may be in the range of meters. There is no limitation to the number of guided mode resonance device 1 that may be arranged in a device or system.

The invention also concerns a gas sensing device 100 comprising a guided mode resonance device 1 as described above. Said gas sensing device 100 is based on the change in absorption of the evanescent portion of the wave guided by the waveguide 30 of the guided mode resonance device 1 of the invention when the concentration of said gas changes. Said gas sensing device, illustrated in FIG. 11, comprises at least a first-type grating structure 22 and a second-type grating structure 24, separated by a portion 35 of a waveguide 30, i.e. by said separation section 35. The length of said portion 35 is adapted to the type of gas that has to be detected. Preferably a thin chemically sensitive dye layer is arranged at least to the waveguide 30 of said guided mode resonance device 1. The portion of the waveguide 30 allows the evanescent portion of the wave guided by said waveguide 30 to interact with said chemically sensitive dye layer. A gas that is present or that flows in direct contact with said chemically sensitive dye layer will change the absorption of said evanescent wave by the chemically sensitive dye layer. This absorption is strongly amplified by the resonance of the guided mode. When said absorption changes, the spectral distribution of the outcoupled light beams of the device will change and may be detected easily. The so produced color effect is a very visible effect because the eye is very sensitive to a relative change of the color of said outcoupled light beams. The change in spectral distribution may of course also be detected by an optical detection system as further explained.

Figure 11:
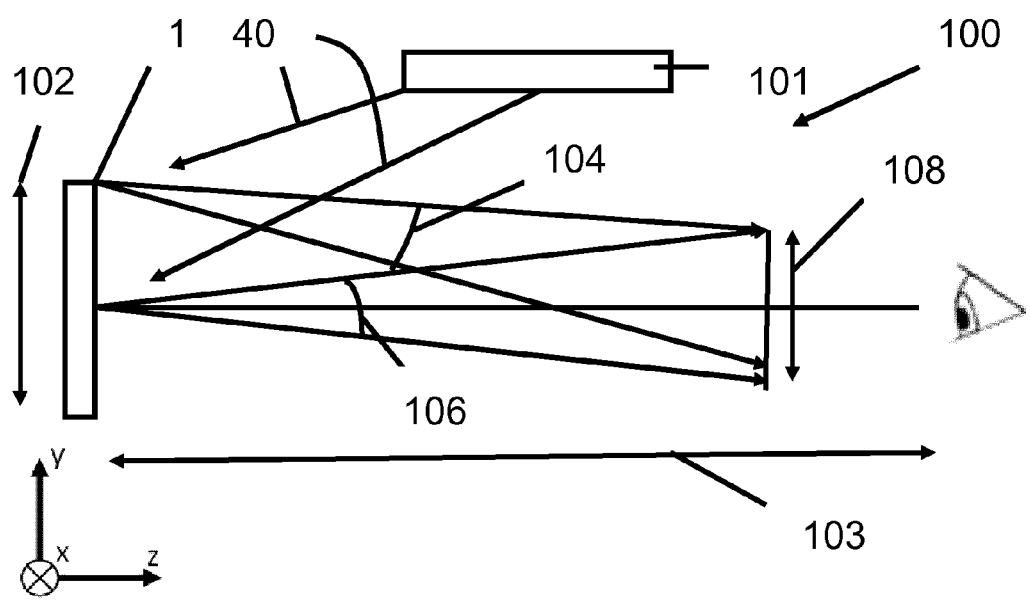
FIG. 11 illustrates a gas sensing device comprising a guided mode resonance device.

A exemplary configuration for a gas sensing device 100 according to the invention is shown in FIG. 11. The gas sensing device, in the embodiment of FIG. 11, comprises a light source 101 and a guided mode resonance device 1. The guided mode resonance device has a chosen lateral dimension 102 and outcoupled beam divergences 104, 106, each provided by said elementary grating structures of the device, such that part of the different out-coupled light beam can converge towards the eye of an observer.

In an embodiment said gas sensing device 100 comprises an optical system to redirect the outcoupled beams of the guided mode resonance device 1 to a detector system, comprising preferably a detector array.

The object of the invention is further achieved by a method to detect a gas or the change of concentration of a gas by using a gas sensing device 100 as described. This method comprises the steps of:
  providing a gas sensing device 100 as described,
  positioning a light source to the side of said grating structures of the gas sensing device 100,
  introducing a gas, or changing the concentration of a gas, between said light source and the guided mode resonance device 1, said gas being arranged to be in contact with said grating structures and said waveguide 30
  observing by the eye or detecting with a photodetector the change of spectral distribution of said first light beam 42 and said second light beam 44.

The invention also concerns a bio-chemical sensing device 120 comprising the guided mode resonance device 1 as described above. Chemical and biochemical sensors are becoming more and more important in everyday life. There is a particular interest in visual sensors that may warn people of any chemical pollution or dangerous chemical and/or biological substances that could harm life. Different chemical system are on the market that change their color when exposed to such bio-chemical substance, for example a pH detection paper which changes its color when the acidity of a liquid changes. There is also an interest in simple and cheap sensors to detect the safety of packaged food for example. The major drawback of detection devices based on pure chemical approaches is their poor sensitivity and the small changes in the optical appearance. The bio-chemical sensing device of the invention allows to improve these limitations. The bio-chemical sensing device 120 of the invention is based on the change of the spectra of said outcoupled beams of a guided mode resonating device, due to a modification of the mode resonances of the guided mode resonance device 1 of the invention. When a bio-chemical reaction takes place at the surface of the waveguide 30 of the guided mode resonance device 1. By changing the refractive index for example, the resonance conditions of the guided mode resonance change and so the spectral distribution of the outcoupled light beams of the device. Also, the resonance of the waveguide 30 grating of the guided mode resonance device 1 of the invention may be used to emphasize the visual effect of a change in the absorption of the evanescent portion of the guided wave in said waveguide 30, due to the interaction of said evanescent wave with said bio-chemical layer in which a bio-chemical reaction takes place. Light absorption within a thin layer arranged to the waveguide 30 of the guide mode resonance device may be considerably amplified by choosing a long said separation section 35 of said bio-chemical sensing device. The amount of the absorbed light depends on the local field amplitude of said evanescent wave, the intrinsic absorption change due to the bio-chemical reaction and the volume of the substances interacting with said evanescent wave.

Figure 12:
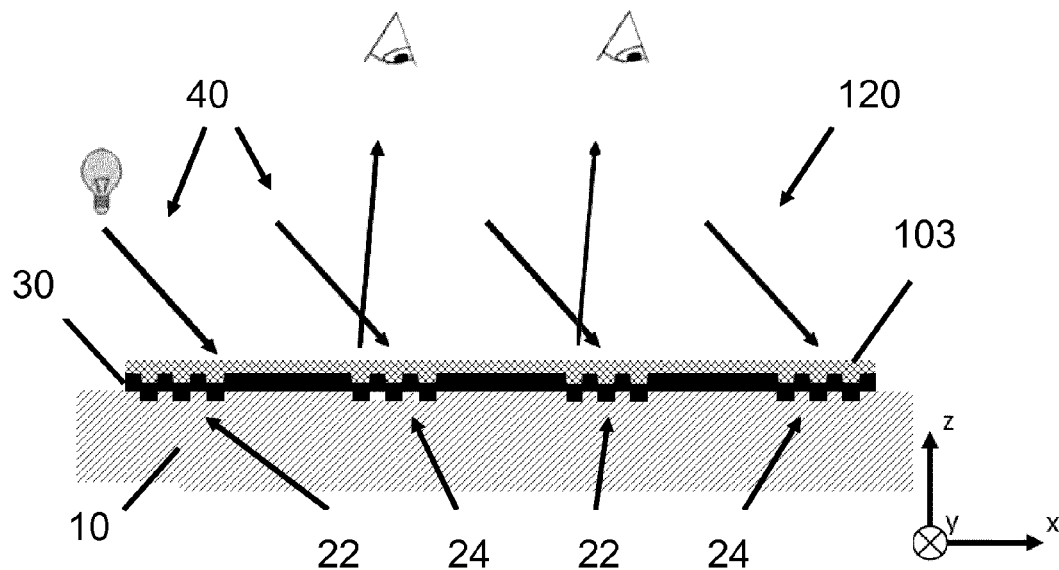
FIG. 12 illustrates a bio-chemical sensor comprising a guided mode resonance device.
Figure 13:
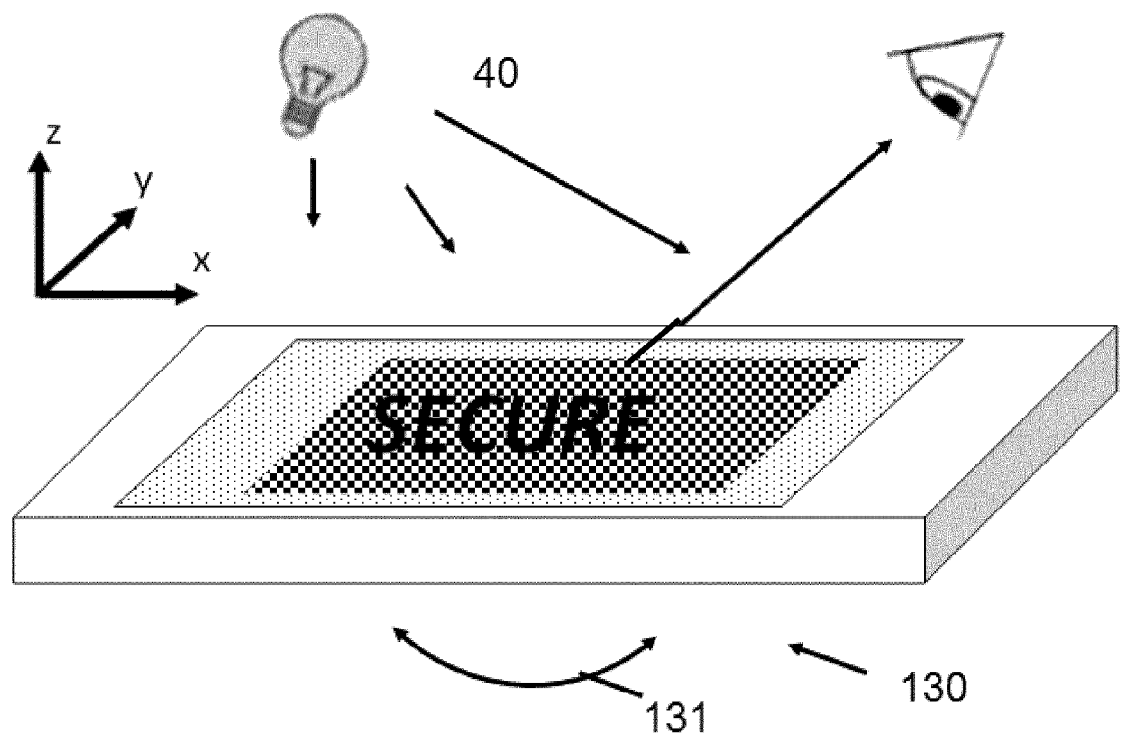
FIG. 13 illustrates a security element comprising a guided mode resonance device.

In an embodiment, illustrated in FIG. 12 said bio-chemical sensing device 120 comprises a bio-chemical layer 121 arranged to the surface of the waveguide 30. A substance applied to said bio-chemical layer may react with said bio-chemical layer 121 and produce a reaction so that the evanescent field of the propagating light 4 in the waveguide 30 is either partially absorbed or that the propagation properties of said evanescent wave changes because of a change of index of refraction of said bio-chemical layer. Said absorption and/or said change of index of refraction change the resonant conditions of the guided mode resonance device 1. Any change of said resonance conditions modifies the spectral characteristics of said at least first and second light beam 44, allowing to detect the bio-chemical reaction. A fixing layer may be arranged to the guided mode resonance device 1, in particular to a portion of the surface comprising a portion of the waveguide 30. Said fixing layer may improve the adherence of a bio-chemical layer to the detection area which is substantially located on said waveguide 30. In an embodiment a polymer layer may be arranged between the bio-chemical layer 121 and the waveguide 30. In a variant a gel may be arranged. Said bio-chemical layer or bio-chemical substance may be arranged or incorporated in said gel.

In an embodiment, the bio-chemical sensing device 120 comprises an optical system to redirect the outcoupled beams of the guided mode resonance device 1. Such a configuration may be similar as the configuration illustrated in FIG. 11.

The invention also concerns a method for sensing of a bio-chemical substance comprising the steps of:
  providing a bio-chemical sensing device 120 as described above,
  positioning a light source to the incident side of said grating structures of the guided mode resonance device 1,
  positioning said bio-chemical substance in contact with said bio-chemical layer to provoke a reaction between said substance and sais bio-chemical layer, observing by the eye, or detecting with a photo detector and appropriate computing means, the change of spectral distribution of said first light beam 42 and said second light beam 44.

Another objective of the invention is achieved by a security device 130 comprising a guided mode resonance device 1 as described above. Said security device 130 project at least two beams having bright colors as observed by the eye. The advantage of such a security device 130 according to the invention is that the initial cost of the equipment to realize the security elements is expensive. So the security element is difficult to counterfeit. The quality of the colors obtained by said security element is superior to what is achieved by security elements of prior art. Special spectral effects may be obtained by said security element, for example by arranging, as explained above, said elementary grating structures 2 in a regular or non-regular 2D arrays.

The specific optically variable effects that can be obtained with the security device 130 of the invention can be distinguished from devices reported in prior art, as the guided mode resonance can be engineered to exhibit very low reflective diffraction of the said incident light beam 40 while exhibiting non-specular variable color effects with the said at least first and/or second outcoupled light beams. Such effects can be designed in the UV and/or visible and/or IR spectral ranges. Realizing a security device 130 with the guided mode resonance device 1 of the invention may be produced with roll-to roll replication techniques and allows fabricating relatively cheap devices, which can be combined with other optical variable devices used in security, having a high degree of security, while their origination techniques and design requires advanced equipment. Such optical security devices based on said guided mode resonance device 1 can be used to protect document of value such as fiduciary document, identity documents, driving or other licenses and goods of value, by enabling their optical control with unique appearance while being difficult to replicate or to forge.

Also, arranging additional structures such as microlenses or additional gratings to the elementary gratings structures, as described above, may improve the difficulty to counterfeit said security device 130. In most applications the security element is observed by the eye and colors are observed by rotating the security device under an angle 132. By changing the angle 132 of the device different colors appear in function of that angle 132. The elementary grating structures of the security device 130 may be arranged so that different color changes appear when rotating the security device in space. Said rotation may be made in the x-y plane, in the y-z plane or in both of said planes In a variant, said security may be inserted in a detection system comprising at least a photodetector and appropriate computing means allowing to analyse the spectral distribution of at least said first lightbeam 22 and said second light beam 44 coupled out of the guided mode resonance device 1 of the security device 130. The security device may be arranged preferably to a document, or to any object whose identification has to be secured and/or controllable.

The invention claimed is:

1. A guided mode resonance device, comprising
   a substrate, defining a substrate plane,
   a thin-film waveguide,
   a sub-wavelength grating structure associated with said waveguide, said grating structure being arranged to an incident surface of said substrate, said incident surface being intended to receive an incident light beam provided by at least one light source, said incident light beam having an incident angle, defined relative to the normal of said waveguide, said grating structure comprising at least one elementary resonant grating structure comprising at least a first-type grating structure and at least a second-type grating structure, wherein:
   said waveguide is arranged to transfer light from the first-type grating structure to the second-type grating structure and also to transfer light from the second-type grating structure to the first-type grating structure,
   said waveguide being made of a material of a refractive index at least 0.05 higher than the refractive index of the material adjacent to the side of the waveguide opposite to the incident surface,
   said first-type grating structure is arranged to incouple into said waveguide a first portion of said incident light beam,
   said second-type grating structure is arranged to incouple into said waveguide a second portion of said incident light beam,
   said first-type grating structure is arranged to couple out, of said waveguide, an outcoupled part of said second portion of said incident light beam, said outcoupled part defining a first light beam,
   said second-type grating structure is arranged to couple out, of said waveguide, an outcoupled part of said first portion of said incident light beam, said outcoupled part defining a second light beam,
   said first light beam and said second light beam having each an outcoupling angle, defined relative to the normal to the waveguide, said outcoupling angle being defined so that said first and second light beam is not symmetric, relative to the normal to the waveguide, to said incident light beam, and not parallel to said incident light beam,
   said first light beam having a different spectral distribution than said second light beam,
   said first-type grating structure and said second-type grating structure having different grating periods and/or a different grating orientation in said substrate plane.

2. The guided mode resonance device according to claim 1 wherein said elementary grating structure comprises two first-type grating structures.

3. The guided mode resonance device according to claim 2 wherein said second-type grating structure is arranged in between said two first-type grating structure, and wherein
   one of said first-type grating structures is arranged to incouple into said waveguide a first portion of said incident light beam,
   one of said first-type grating structures is arranged to couple out, of said waveguide, an outcoupled part of said second portion of said incident light beam, said outcoupled part defining a first light beam.

4. The guided mode resonance device according to claim 1, wherein the material of said waveguide is selected from the group consisting of $TiO_2$, $HfO_2$, $Ta_2O_5$, $ZrO_2$, AlN, $Al_2O_3$, ZnO, $SiO_2$, Si, $Si_3N_4$, $MgF_2$, $CaF_2$, MgO, and combinations thereof.

5. The guided mode resonance device according to claim 1, wherein said grating structure is arranged on the substrate plane facing said incident light beam.

6. The guided mode resonance device according to claim 1, wherein an intermediate layer is arranged between said substrate and said grating structure.

7. The guided mode resonance device according to claim 1, wherein said first light beam and said second light beam have an outcoupling angle differing by more than 10° than said incident angle.

8. The guided mode resonance device according to claim 1, comprising an array of said elementary grating structures, said array comprising at least two elementary grating structures, each elementary grating structure of said array being arranged to cooperate with adjacent said elementary grating structures.

9. The guided mode resonance device according to any claim 1, wherein said elementary structures are arranged in a two dimensional array.

10. The guided mode resonance device according to claim 9 wherein said array comprises non-parallel rows of elementary structures.

11. The guided mode resonance device according to claim 1, wherein said elementary structures further comprise at least one further optical structure.

12. A gas sensing device comprising a guided mode resonance device according to claim 1, wherein the guided mode resonance device is arranged so that the spectral distribution of said first light beam and/or said second light beam is modified by a change of the concentration of said gas.

13. A bio-chemical sensing device of a bio-chemical substance comprising a guided mode resonance device according to claim 1, further comprising a bio-chemical layer designed for reacting with said biochemical substance, said bio-chemical layer being arranged in contact with said waveguide and/or said grating structure, and wherein said biochemical sensing device is arranged so that the spectral distribution of said first light beam and/or said second light beam is modified by the reaction of said bio-chemical substance with said bio-chemical layer.

14. A method for sensing of a bio-chemical substance comprising the steps of:
  providing a bio-chemical sensing device according to claim 13,
  positioning a light source to the side of said grating structures of the guided mode resonance device,
  positioning said bio-chemical substance in contact with said bio-chemical layer for provoking a reaction between said substance and sais bio-chemical layer,
  observing by the eye or detecting with a photo detector the change of spectral distribution of said first light beam and said second light beam.

15. A security device comprising a guided mode resonance device according to claim 1.

* * * * *

UNITED STATES PATENT AND TRADEMARK OFFICE
CERTIFICATE OF CORRECTION

PATENT NO. : 9,946,019 B2
APPLICATION NO. : 15/106723
DATED : April 17, 2018
INVENTOR(S) : L. Davoine et al.

It is certified that error appears in the above-identified patent and that said Letters Patent is hereby corrected as shown below:

In the Claims

| Column | Line | Error |
|---|---|---|
| 22 (Claim 14, Line 9) | 19 | "sais bio-chemical" should read --said bio-chemical-- |

Signed and Sealed this
Twenty-sixth Day of March, 2019

Andrei Iancu
*Director of the United States Patent and Trademark Office*